US007005460B2

(12) United States Patent
Bublewitz et al.

(10) Patent No.: US 7,005,460 B2
(45) Date of Patent: Feb. 28, 2006

(54) TWO-STEP CURABLE MIXER-SUITABLE MATERIALS

(75) Inventors: Alexander Bublewitz, Herborn (DE); Jens-Peter Reber, Herborn (DE); Ulrich Nagel, Tübingen (DE)

(73) Assignee: Kettenbach GmbH & Co. KG, Eschenburg (DE)

(*) Notice: Subject to any disclaimer, the term of this patent is extended or adjusted under 35 U.S.C. 154(b) by 0 days.

(21) Appl. No.: 10/053,878

(22) Filed: Jan. 24, 2002

(65) Prior Publication Data

US 2002/0156186 A1 Oct. 24, 2002

Related U.S. Application Data

(63) Continuation-in-part of application No. 09/808,412, filed on Mar. 15, 2001, now abandoned.

(30) Foreign Application Priority Data

Jan. 25, 2001 (DE) ........................................ 101 03 446

(51) Int. Cl.
*C08L 83/00* (2006.01)

(52) U.S. Cl. ....................... 523/109; 525/477; 525/478; 525/479; 528/15; 528/31; 528/32; 524/95; 524/306; 524/425; 524/430; 524/431; 524/432; 524/436; 524/437; 524/448; 524/450; 524/451; 524/588

(58) Field of Classification Search ................... 528/15, 528/17, 18, 31, 32; 525/477, 478, 479; 524/95, 524/306, 425, 430, 448, 450, 451, 588
See application file for complete search history.

(56) References Cited

U.S. PATENT DOCUMENTS

| | | | | | |
|---|---|---|---|---|---|
| 4,754,013 | A | * | 6/1988 | Antonen | 528/15 |
| 5,321,082 | A | * | 6/1994 | Ohsugi et al. | 525/101 |
| 5,684,110 | A | * | 11/1997 | Kawamura | 528/15 |
| 5,696,209 | A | * | 12/1997 | King et al. | 525/478 |
| 5,792,881 | A | | 8/1998 | Wolter et al. | |
| 5,945,475 | A | * | 8/1999 | Yamada et al. | 524/588 |
| 6,013,711 | A | | 1/2000 | Lewis et al. | 524/265 |
| 6,187,890 | B1 | | 2/2001 | Fehn et al. | 528/15 |
| 6,201,055 | B1 | * | 3/2001 | Lutz et al. | 524/493 |
| 6,222,055 | B1 | | 4/2001 | Wolter et al. | |
| 6,313,190 | B1 | | 11/2001 | Bublewitz et al. | 523/109 |
| 6,348,557 | B1 | | 2/2002 | Barthel et al. | |
| 6,359,098 | B1 | | 3/2002 | Fehn et al. | 528/15 |
| 6,403,751 | B1 | | 6/2002 | Engelbrecht et al. | |

FOREIGN PATENT DOCUMENTS

| | | | |
|---|---|---|---|
| EP | 01 410 199 | B1 | 1/1991 |
| EP | 0 576 112 | A1 | 12/1992 |
| EP | 0 664 322 | B1 | 7/1998 |
| EP | 0 718 432 | B1 | 10/2002 |

* cited by examiner

*Primary Examiner*—Margaret G. Moore
*Assistant Examiner*—Marc S. Zimmer
(74) *Attorney, Agent, or Firm*—Collard & Roe, P.C.

(57) ABSTRACT

The present invention relates to a multi-component system for making impressions which contains (a) at least one compound having at least two alkenyl groups;

Figure 1:
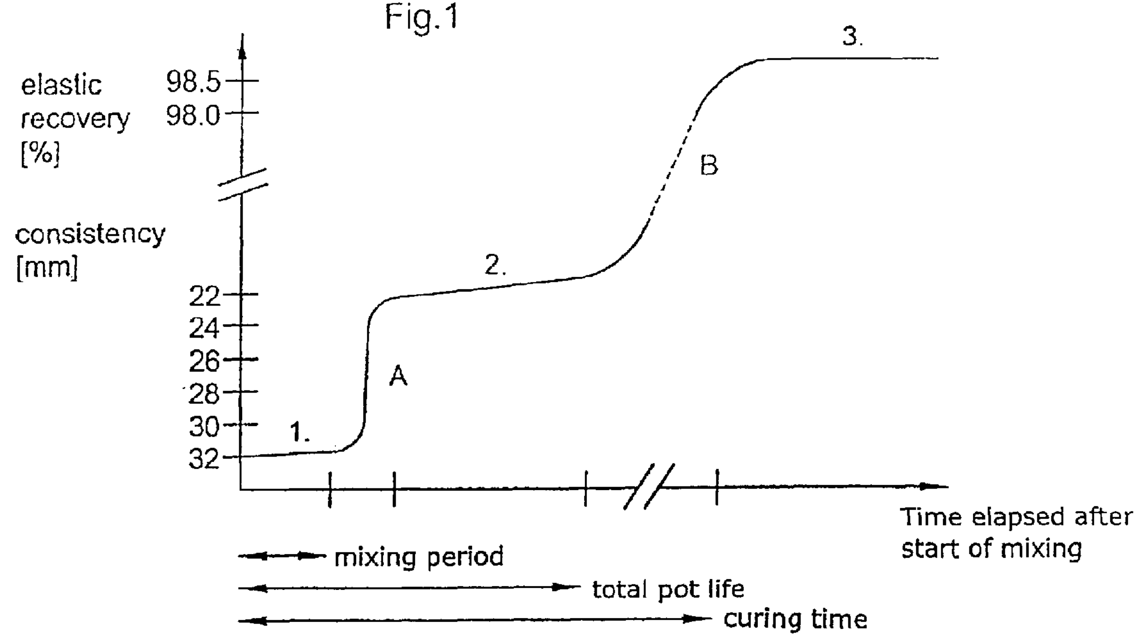

(b) at least one organohydrogenpolysiloxane;

(c) at least one hydrosilylation catalyst;

characterized by containing (d1) at least one polymeric compound having at least one alkynyl group and/or (d2) at least one compound having at least one Si—OR structural unit, wherein R=H, alkyl, alkoxyalkyl or acyl; and when a compound (d2) having at least one Si—OR structural unit is contained, (e) at least one condensation catalyst and/or condensation cross-linking agent.

After the mixing of the components, the materials according to the invention cure in two steps. At the beginning of mixing, the mixture, in a first state, has a mixer-suitable consistency, whereupon the mixture undergoes transition to a heavier-bodied second state due to condensation reactions of SiOR groups and/or hydrosilylation reactions of alkynyl groups with SiH groups, followed by transition to a third solid, elastic state following curing through a hydrosilylation reaction of alkenyl groups with SiH groups. The invention also relates to mixtures and components comprising further ingredients, as well as methods for the preparation of impressions.

24 Claims, 1 Drawing Sheet elastic
recovery
[%]
98.5
98.0
consistency
[mm]
22
24
26
28
30
32
1.
A
2.
B
3.
Time elapsed after
start of mixing
mixing period
total pot life
curing time elastic
recovery
[%]
98.5
98.0
consistency
[mm]
22
24
26
28
30
32
1.
C
2.
Time elapsed after
start of mixing
mixing period
total pot life
curing time

TWO-STEP CURABLE MIXER-SUITABLE MATERIALS

This is a continuation-in-part of U.S. Ser. No. 09/808,412 filed Mar. 15, 2001, now abandoned.

The present invention relates to multicomponent systems, components, mixtures and methods for making impressions.

Addition-cross-linkable silicones make use of the hydrosilylation, catalyzed by a (precious) metal (A), between a vinyl-end-stopped polydimethylsiloxane (B) and a polymethylhydrogensiloxane (C) to build a three-dimensional elastomeric network. This involves adding the SiH group of the polymethylhydrogensiloxane to the Si-vinyl group to form an ethylene bridge. Once the components A, B and C are brought into contact, the cross-linking reaction starts immediately. In order to provide user-oriented processing conditions, addition-cross-linkable silicones are stored as two-component materials in the form of separated components 1 and 2 and mixed together only shortly before use.

In addition to the vinylorganopolysiloxanes (B), component 1 contains the (precious) metal catalyst (A) (usually a platinum catalyst) necessary for the cross-linking reaction. Component 2 necessarily contains polymethylhydrogensiloxane (C) as a cross-linking agent and optionally vinylorganopolysiloxane.

For adjusting the pot life of these addition-cross-linkable two-component silicones, so-called inhibitors are employed which interfere in the catalytic cycle and thus control the reaction rate.

Examples of those inhibitors mentioned above are benzotriazole, ethynylcyclohexanol, short-chained vinyl-containing organopolysiloxanes, such as divinyltetramethyldisiloxane, and vinyl-containing cyclic siloxanes, such as tetravinyltetramethylcyclotetrasiloxane, diethyl maleate and n-octylsilane ($C_8H_{17}SiH_3$).

In addition, as in DE 19837855 A1 or WO 97/40102, for example, short chain alkynyl compounds or dialkynyl compounds are used which complex or chelate the platinum catalysts.

The cross-linking of the addition-cross-linkable silicones through hydrosilylation is very sensitive towards catalyst poisons, such as nitrogen, phosphorus or sulfur compounds, as occur in organic compounds, such as amino acids, or in latex gloves, for example. This means that the curing reaction is decelerated upon contact with such catalyst poisons, or even brought to subside in the worst case.

In technology, addition-cross-linkable silicones are widely employed for use as impression materials (e.g., in model-making), casting compositions for the electrical and automobile industries, and sealants for the construction and automobile industries (see Andreas Tomanek, "Silicone und Technik", 1990, Hanser Verlag München; W. Noll, "Chemie und Technologie der Silicone", 1968, Verlag Chemie; "Silicone: Chemie und Technologie", 1989, Vulkan Verlag, Essen).

In dentistry, addition-cross-linkable silicones are successfully employed for making dental impressions, for checkbite recording and for the relining of dental prostheses.

When they are used as a material for making dental impressions, different shaping techniques can be employed:

- monophase shaping (one phase and one time);
- sandwich technique (two phases and one time);
- dual mixing technique (two phases and one time);
- correction shaping (two phases and at two different times).

In the sandwich and correction shaping techniques, two silicone impression materials having different mixing consistencies (ISO 4823) are employed.

In the first step, the impression tray is charged with a kneadable support material (putty), which, in a second step, is covered with a layer of a light-bodied silicone. In the sandwich technique, this is done simultaneously during the pot life of the two materials, followed by simultaneously applying the two materials in the patient's mouth.

In correction shaping, the kneadable putty material is made to cure as a preimpression material in the patient's mouth, trimmed after removing from the mouth, and in a second subsequent step, it is covered with a layer of a light-bodied material and again made to cure in the patient's mouth.

According to the prior art (Dr. Bernd Wörtmann, Habilitationsschrift 1992, "Zum derzeitigen Stand der Abformung in der Zahnheilkunde", University of Münster, Germany; J. Wirz, "Abformungen in der zahnärztlichen Praxis", 1993, Gustav Fischer Verlag), the support material (putty) is predominantly employed in the form of a kneadable material. This has the advantage that a higher back pressure is generated in the impression tray when the impression is made. In the sandwich technique, this causes the light-bodied correction material to flow into narrow cavities and the sulcus to ensure a highly precise shaping down to details.

When the preimpression for the correction shaping material is made, the kneadable support material, due to its viscous consistency, has the advantage of spreading less finely and thus reserving more space for the subsequent correction shaping steps using the light-bodied material.

In order to provide additional space for the correction material employed in the subsequent step, it may be necessary to trim the cured support material, i.e., in the preimpression, the shaped interdental spaces are cut off, and drainage channels are laid down.

This is the reason why the cured support material must be easy to trim, e.g., using a scalpel.

Otherwise, the support material would be deformed in this step (Prof. Dr. Wöstmann, University of GieBen, Germany: "Zum derzeitigen Stand der Abformung in der Zahnheilkunde", Münster 1992).

However, the user of the support material (putty) used for the above mentioned shaping techniques must face the following disadvantages:

Dosage is effected with dosing spoons by means of which the kneadable material is removed from the storage cans clumsily and with a relatively high expenditure of force. Subsequently, the components, which are differently colored, are kneaded into a homogeneous compound using a mixing fork or manually. This procedure is also more or less complicated and, when a kneading fork is used, requires a high expenditure of force. This way of dosing and mixing may involve the following errors:

- there is a risk of wrong dosage; and
- there is a risk of non-homogeneous mixing of the two components.

Both factors lead to insufficient cross-linking so that the precision of model making is no longer ensured.

The dosing of kneadable preimpression materials (putties) involves the risk of contamination of the components with the respectively other component. From former experience, it is known that application errors cannot be avoided in spite of the color coding.

The dosing spoons or the covers of the containers of components 1 and 2 are often confused by the user, or he reaches into the storage can with contaminated fingers or gloves. Impression materials thus contaminated are no longer suitable for further use; for example, they contain cured regions in the form of lumps.

In the usual mixing of kneadable preimpression materials (putties) by hand, there is a risk that catalyst poisons may be extracted from the user's skin or protective gloves, which may lead to deceleration of the curing or even prevent curing of the impression material in the worst case.

In the market, so-called putty cartridge materials (e.g., Reprosil Quixx Putty, Dentsply Caulk) are known which can be processed with the commercially available mixing and dosing systems and which can be employed as an alternative of kneadable preimpression materials. These are light- to heavy-bodied materials according to ISO 4823, which exhibit a relatively high degree of cross-linking already during their pot life due to their rapid cross-linking characteristic. Consequently, the originally light- to heavy-bodied initial consistency is highly increased during the pot life and the user experiences the feeling of a putty material (high pressure) when the impression is being made.

These impression materials have the disadvantage that their total pot life to be used by the dentist is highly limited. When the predetermined pot lives are exceeded or when the ambient temperatures are slightly increased, there is a risk that the impression material has already formed large elastic fractions or, in an extreme case, has already cured so that the impressions are highly distorted by endogenous strains, restoring forces and compressions and are thus useless.

It has been the object of the present invention to provide mixer-suitable impression materials based on addition-cross-linkable polydimethylsiloxanes which, due to their light- to heavy-bodied mixing consistency in the initial phase, can be dispensed from the recently developed automatic mixing and dosing systems and, due to their two-step reaction mechanism, undergo transition to a second mixing consistency with increased viscosity in a first reaction step after the mixing period.

In a second reaction step after a presettable pot life during which an impression is made, the impression material is to cure completely to an elastic final state in which a shaping result is recorded.

"Mixer-suitable impression material" means a multicomponent impression material which can be dispensed, for example, from a two-component disposable cartridge through a static mixer, e.g., of Mixpac (Keller EP 0 615 787 A1, EP 0 730 913 A1) or from tubular film bags in dual-chamber reusable cartridges through a dynamic mixer, e.g., in the "Mixstar" device of DMG-Mühlbauer (PCT/EP 98/01993 and PCT/EP 98/01858) or in the "Pentamix I" and "Pentamix II" devices of Espe (EP-A-0 492 413 and EP-A-0 492 412).

The requirement of mixer-suitability can be met by impression materials which, at the beginning of the mixing period, are in a consistency range of larger than 26 mm, especially larger than 30 mm, according to ISO 4823.

It has been the object of the present invention to provide an impression material which avoids the drawbacks set forth above and to provide a method which permits the preparation of impressions in a simple and reliable way from objects from which impressions are to be made. In particular, the object has been to provide a multi-component impression material which can be simply and readily mixed and is mixer-suitable, suitable for making impressions and undergoes transition to an elastic solid state.

These objects are surprisingly achieved by providing a multi-component system for making impressions which contains (a) at least one compound having at least two alkenyl groups;

(b) at least one organohydrogenpolysiloxane;

(c) at least one hydrosilylation catalyst;

characterized by containing (d1) at least one polymeric compound having at least one alkynyl group and/or (d2) at least one compound having at least one Si—OR structural unit, wherein R=H, alkyl, alkoxyalkyl or acyl; and when a compound (d2) having at least one Si—OR structural unit is contained, (e) at least one condensation catalyst and/or condensation cross-linking agent.

It is preferred to provide a multi-component system for making impressions comprising at least two components A and B, wherein component A contains (a) at least one compound having at least two alkenyl groups; and (b) at least one organohydrogenpolysiloxane; and (d1) at least one polymeric compound having at least one alkynyl group and/or (d2) at least one compound having at least one Si—OR structural unit, wherein R=H, alkyl, alkoxyalkyl or acyl;

and component B contains (c) at least one hydrosilylation catalyst; and when a compound (d2) having at least one Si—OR structural unit is contained, component A and/or B contains (e) at least one condensation catalyst and/or condensation cross-linking agent.

Compounds (a), (b) and (d1) are individual compounds. Component A and/or B according to the invention may additionally contain (f) inhibitors of the condensation reactions of condensation catalysts and/or condensation cross-linking agents with compounds containing Si—OH structural units, wherein R=H, alkyl, alkoxyalkyl or acyl;

(g) water-donating agents;

(h) desiccants;

(i) inert carrier materials;

(j) compounds for reaction inhibition of the hydrosilylation reaction;

(k) reinforcing fillers;

(l) non-reinforcing fillers and/or (m) auxiliaries.

The object of the invention is achieved by making use of a two-step reaction mechanism which is initiated during and upon mixing of components A and B and which relies on the different reactivities in the addition cross-linking of the alkenyl and alkynyl groups towards SiH groups and/or relies on the different reaction mechanisms in the addition cross-linking between alkenyl and SiH groups as compared to the condensation cross-linking of Si—OR groups, wherein R=H, alkyl, alkoxyalkyl or acyl, with condensation catalysts.

Surprisingly, in the combination of the hydrosilylation reactions of Si-vinyl and Si-ethynyl groups, it is found that a) the reactions proceed in successive periods of time and are thus suitable for use in two-step curable impression materials;

b) in a multicomponent, especially two-component, material, the reactants can be distributed on the individual components, e.g., in a dual-chamber cartridge or tubular film bag, in such a way that these are storage-stable at room temperature over a period of at least 12 months, i.e., do not exhibit any losses in reactivity.

Surprisingly, when the condensation reaction (hydroxypolysiloxane with condensation catalysts, such as titanic acid ortho esters) is combined with the hydrosilylation reaction (Si-vinyl and/or Si-ethynyl with organohydrogenpolysiloxanes in the presence of Pt catalysts), it is found that a) the reactions proceed in successive periods of time when suitable inhibitors are employed;

b) the reactions proceed independently, without the reactants having a negative effect on the reactivity of the respective other reactions;

c) in a multicomponent, especially two-component, material, the reactants can be distributed on the individual components, e.g., in a dual-chamber cartridge or tubular film bag, in such a way that these are storage-stable at room temperature over a period of at least 12 months, i.e., do not exhibit any losses in reactivity or deterioration of mechanical properties in the cured product;

d) the concentration range of the metal alkoxides employed can be selected in such a way that in practice, i.e., when used in cartridges and tubular film bags, obstruction of the exit channels due to “silicification” from access of atmospheric moisture does not occur.

The components are preferably selected in such a way that the condensation and hydrosilylation reactions occur at from 10 to 40° C., so that the reactions can be performed, in particular, at oral and room temperature.

The alkynyl compounds (d1) used according to the invention are polymeric (long chain) compounds. This is because the viscosity of the mixture is to increase significantly in a relatively quickly proceeding first reaction in which the alkynyl compound reacts with Si—H compounds. This is achieved only if the alkynyl compound has a certain chain length. Therefore, “polymer” as used according to the invention means: If the alkynyl compound is essentially a polysiloxane, compounds having at least 20, preferably 50 and more preferably 500 Si—O units can be used, for example. If the alkynyl compound is essentially a hydrocarbon compound, those having at least 15, preferably 20 and more preferably 25 carbon atoms are preferred, for example. Generally, hydrocarbon compounds increase viscosity more highly than polysiloxane compounds of comparable length do. The proportion of alkynyl compounds in the impression material is preferably at least 1%, more preferably at least 2 or 5%.

The concentration of the alkynyl compound and the chain length of the alkynyl compound are in a reciprocal relationship when the mixture is selected. The longer the chain length, the lower the concentration of the alkynyl compound must be selected. Conversely, the desired increase in viscosity can be achieved when a relatively high concentration of a polymeric alkynyl compound having a relatively short chain length is selected.

In this context, short chain dialkynyl compounds as used as inhibitors for the chelating of Pt or other metals in the prior art (e.g., DE 19837855 A1) cannot be employed according to the invention. Preferred chain lengths of such inhibitors are $C_6$ to $C_8$ because a good chelating effect is achieved in this case only. Due to the short chain lengths, such inhibitors could not cause any significant increase in viscosity.

In preferred embodiments, the alkynyl compound (d1) of component A is

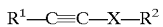

and the Si—OR compound according to (d2) is

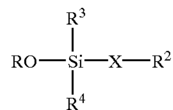

wherein

R=H, alkyl, alkoxyalkyl or acyl;

$R^1$=alkyl, aryl, arylalkyl, halogen-substituted alkyl and aryl groups, cyanoalkyl, cycloalkyl, cycloalkenyl, especially —H, —OH and —OR, and combinations thereof;

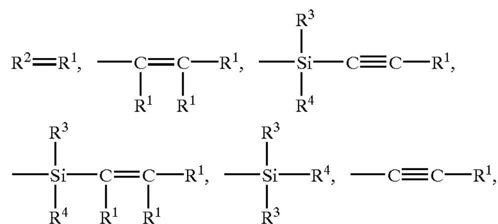

$R^3$=alkenyl, alkynyl, halogen, aryl, alkylaryl, H, halogen-substituted alkyl and aryl groups, especially alkyl, alkoxy and hydroxy, and combinations thereof;

$R^4$=$R^3$, or $R^4$ is different from $R^3$, wherein $R^4$ is, in particular, alkoxy, hydroxy, alkyl, methyl, alkynyl, ethynyl, or combinations thereof; and X=polysiloxane, oligosilicic acid esters, polysilicic acid esters, polyethers, polymeric hydrocarbons, polyesters and copolymers of the above mentioned compounds.

In the polymers, polymeric side chains and/or the residues $R^1$ and/or $R^2$ may be present. The chain may contain alkenyl or alkynyl groups.

Compounds in which R=alkyl, alkoxyalkyl or acyl are preferably employed when Sn catalysts are contained.

As compounds according to (d1) or (d2), component A may contain, in particular, those of the structural formula

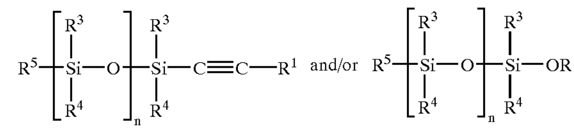

wherein n=7 to 6000, preferably 20 to 6000, more preferably 100 to 6000; R and $R^1$ to $R^4$ are as defined above; and $R^5$=—C≡C—$R^1$, H, alkyl, aryl, $$-\overset{R^1}{\underset{}{C}}=\overset{R^1}{\underset{}{C}}-R^1,$$

alkylaryl, halogen, OH, halogen-substituted alkyl and aryl groups, —OR, aminoalkyl, epoxy, cyanoalkyl, cycloalkyl, alkylhydroxyl, methacrylate, acrylate, mercaptoalkyl, carboxylate, carboxyalkyl or succinic anhydride.

Such compounds can be prepared by methods known from EP 0 639 622 B1, EP 0 959 095 A2, EP 0 926 206 A2, DE 19822679 A1 and DE 19757308 A1.

Preferred alkenyl compounds (a) of component A are those having the structure

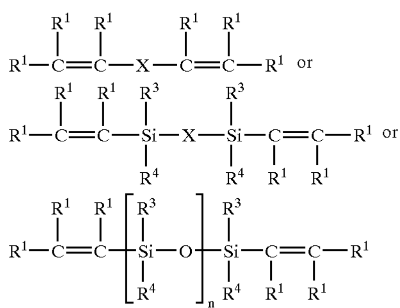

wherein n=0 to 6000; and residues $R^1$, $R^2$, $R^3$, $R^4$ and X are selected as set forth above.

The preferred alkenyl compound (a) may also be a silane dendrimer with terminal alkenyl groups.

Preferred organohydrogenpolysiloxanes (c) contained in component A include polyalkyl-, polyaryl- and polyalkylaryl-, polyhaloalkyl-, polyhaloaryl- or polyhaloalkylarylsiloxanes. They may be in the form of oligomers or polymers in a linear, branched or cyclic form or as a QM resin and have at least one Si—H bond.

Condensation catalysts and/or condensation cross-linking agents (d) preferably employed in component B include aluminum alkoxides, antimony alkoxides, barium alkoxides, boron alkoxides, calcium alkoxides, cerium alkoxides, erbium alkoxides, gallium alkoxides, silicon alkoxides, germanium alkoxides, hafnium alkoxides, indium alkoxides, iron alkoxides, lanthanum alkoxides, magnesium alkoxides, neodymium alkoxides, samarium alkoxides, strontium alkoxides, tantalum alkoxides, titanium alkoxides, tin alkoxides, vanadium alkoxide oxides, yttrium alkoxides, zinc alkoxides, zirconium alkoxides, titanium or zirconium compounds, especially titanium and zirconium alkoxides, and chelates and oligo- and polycondensates of the above alkoxides, dialkyltin diacetate, tin(II) octoate, dialkyltin diacylate, dialkyltin oxide and double metal alkoxides. Double metal alkoxides are alkoxides containing two different metals in a particular ratio. In particular, the following are employed: titanium tetraethylate, titanium tetrapropylate, titanium tetraisopropylate, titanium tetrabutylate, titanium tetraisooctylate, titanium isopropylate tristearoylate, titanium truisopropylate stearoylate, titanium diisopropylate distearoylate, zirconium tetrapropylate, zirconium tetraisopropylate, zirconium tetrabutylate. In addition, titanates, zirconates and hafnates as described in DE 4427528 C2 and EP 0 639 622 B1 can be used.

Hydrosilylation catalysts (c) preferably employed in component B include transition metals of the 8th auxiliary group, especially platinum, palladium and rhodium or their salts, complexes and colloids, preferably platinum complexes and salts of hexachloroplatinic acid, especially platinum(0)-1,3-divinyl-1,1,3,3-tetramethyl-disiloxane complex.

Inhibitors of the condensation reactions (f) preferably employed in component A include di-, tri-, oligo- and polydialkylsiloxanes of general formula $$Z—SiR_2—O—(SiR_2O)_n—SiR_3 \text{ or}$$

$$Z—SiR_2—O—(SiR_2O)_n—SiR_2—Z,$$

wherein Z═OH or $NR_2$, R represents the same or different optionally substituted hydrocarbyl residues, such as alkyl, alkenyl, aryl or alkynyl, and n=0 or an integer of from 1 to 100.

Further, aliphatic diols, diamines, diphosphanes, polyamines, polyphosphanes or polyols, OH-, NH- or PR-functional polyethers or other chelating compounds may be employed.

Water-donating agents (g) preferably employed in component A include inorganic fillers containing superficially bound residual moisture or water bound in the crystal lattice, zeolites or purposefully moistened fillers or organic substances having a defined water content.

Preferred desiccants (h) in components A and/or B are zeolites, dried fillers or water-absorbing organic compounds, such as oxazolidines and alkali salts of poly(meth)acrylic acid (superabsorbers).

Inert carrier materials (i) preferably used include mineral oils, branched hydrocarbons, vaseline, esters, phthalic acid esters, acetyltributyl citrate, polyalkylene oxides and polyesters and their copolymers.

Compounds for reaction inhibition of the hydrosilylation reaction (j) preferably employed include short-chained organopolysiloxanes of general formula $$CH_2═CH—SiR_2O—(SiR_2O)_n—SiR_2—CH═CH_2,$$

wherein R represents the same or different optionally substituted hydrocarbyl residues, such as alkyl, alkenyl, aryl, alkynyl, alkenyl, and alkynyl-terminated siloxane residues; and n=0 or an integer of from 1 to 6.

Vinyl-containing cyclic siloxanes, such as tetravinyltetramethylcyclotetrasiloxane, or organic hydroxy compounds containing terminal double or triple bonds, diethyl maleate, alkylsilane, arylsilane, alkenylsilane, alkynylsilane, benzotriazole, compounds comprising a 1,4-ene-yne structural unit, compounds comprising a 1,3-ene-yne structural unit, such as 2-methyl-1-hexene-3-yne, ethyl-3-(trimethylsilyl)propynoate, bis(phenylethynyl) dimethylsilane, diynes, such as decadiyne or dodecadiyne, polyynes, dienes, polyenes, such as decatriene, (1,3-dioxane-2-ylethynyl)trialkylsilane, 1,4-divinyltetramethyldisilylethane, amines or phosphanes can also be employed.

Reinforcing fillers (k) preferably employed in components A and/or B include highly dispersed active fillers, such as titanium dioxide, aluminum oxide, zinc oxide, preferably wet-precipitated or pyrogenic silicic acid, which may be in a hydrophilic or hydrophobized form; or mineral fibrous fillers, such as wollastonite, or synthetic fibrous fillers, such as glass gibers, ceramic fibers or plastic fibers. The BET surface area of these substances is preferably >50 $m^2/g$.

Non-reinforcing fillers (I) preferably employed in components A and/or B include metal oxides, metal oxide hydroxides, mixed oxides or mixed hydroxides, preferably silica, especially in the form of quartz and its crystalline modifications, fused silica, alumina, calcium oxide, aluminum hydroxide, calcium carbonate, kieselguhr, diatomaceous earth, talcum, ground glasses and plastic-based fillers, for example, polymethyl methacrylate, polycarbonate, polyvinyl chloride, silicone resin powder, or powder based on fluoro-organic compounds, the non-reinforcing fillers also being employed in a surface-treated (coated) form. The surface treatment may be done, for example, with silanes and fatty acids which may contain functional groups (e.g., vinyl, allyl, —SiH). Also useful as non-reinforcing fillers are organic or inorganic hollow spheres, solid spheres and fibers. Solid or hollow plastic particles, e.g., also in spherical shapes, on the surface of which inorganic filler articles are embedded, may also be employed. Preferably, the BET surface area of the non-reinforcing fillers is <50 $m^2/g$.

Preferred auxiliaries (m) which may be contained in components A and/or B include dyes, surfactants, opaque substances, matting agents, such as titanium dioxide or zinc oxide, plasticizers, hydrogen adsorbers/absorbers, radiopaque substances or organosilicon MQ resins comprising Si-vinyl, Si—OH, Si—OR, Si-ethynyl and/or SiH groups.

The impression material may have hydrophilic properties, e.g., when surfactants are added as auxiliary agents, or when polyether groups are contained.

Substances for adjusting the pH range may also be contained in components A and/or B. These preferably include acetic acid, citric acid, acetyltributyl citrate, ascorbic acid, acidic reinforcing or non-reinforcing fillers, acidic buffer systems, such as acetic acid/sodium acetate buffers or citric acid/citrate buffers, and alkaline reinforcing or non-reinforcing fillers, such as aluminum hydroxide, alkaline buffer systems, such as carbonate/hydrogencarbonate buffers, or alkaline or acidic ion-exchange resins.

The invention also relates to a mixture of the components. After the mixing of the components, the mixture according to the invention, in a first step, undergoes a transition from a lighter-bodied mixer-suitable initial consistency to a heavier-bodied plastic phase in which the material builds up a high force pressure in the making of dental impressions in the impression tray, and in a second step, cures to its final elastic form.

Preferred mixtures according to the invention have a mixer-suitable consistency, in a first state at the beginning of mixing, of >26 mm, preferably >30 mm (according to ISO 4823), whereupon the mixtures undergo transition to a heavier-bodied second state with a consistency of <35 mm, preferably <30 mm (according to ISO 4823), caused by condensation reactions of SiOR groups and/or by hydrosilylation reactions of alkynyl groups with SiH groups. This latter consistency is maintained over a period of at least 15 s, preferably at least two minutes. Thereafter, the mixtures undergo transition to a third solid, elastic state following curing through a hydrosilylation reaction of alkenyl groups with SiH groups. The above reaction sequence can also be passed in reversed order.

For the two-step curable materials according to the invention, this means that the first reaction step, i.e., the transition from the mixer-suitable consistency of >26 mm, especially >30 mm, to a heavier-bodied consistency of <35 mm, especially <30 mm, can be time-controlled in such a way that the decrease in consistency (viscosity increase) takes place during and after the mixing period according to ISO 4823. The material according to the invention is advantageously discharged directly after mixing when the first reaction has not proceeded, or only so to a low extent. In this way, for example, static or dynamic mixers of manual mixing or dosing systems do not become obstructed, for example, with kneadable impression material. Then, only after leaving the mixer, the significant viscosity increase occurs through the first reaction step of the two-step reaction mechanism. However, when the material according to the invention is selected in such a way that the material of higher viscosity can still be discharged after completion of the first reaction step, the discharging may also be effected during or after completion of the first reaction step.

Preferably, the two individual components A and B have consistencies of >26 mm, especially >30 mm. Thus, it is achieved that the mixture of the two components has a consistency of >26 mm, especially >30 mm, immediately after the beginning of mixing, i.e., when the first reaction has not yet started, or only insignificantly so. On the other hand, one of the two components may also have a lower consistency, and the other component a higher consistency, when both components are matched in such a way that a consistency of the mixture of >26 mm, especially >30 mm, prevails immediately after the beginning of mixing.

The invention encompasses the multicomponent mixtures after mixing, in a described states, and after curing. The mixture in the third, i.e., cured, state preferably meets the requirements demanded of an elastomeric impression material in the cured state according to ISO 4823, such as elastic recovery.

The change of consistency of a multicomponent mixture according to the invention is illustrated in FIG. 1 in an idealized form:

In FIG. 1, the consistency in mm according to ISO 4823 is plotted against the time elapsed after the mixing of components A and B. From the kinetics, two reaction steps A and B and three consistency states, which are relatively stable over some period of time, can be clearly distinguished:

1) 1st state, mixer-suitable consistency after the beginning of the mixing process;
2) 2nd state, heavy-bodied or putty consistency until the end of the total pot life according to ISO 4823. In this 2nd state, the consistency remains almost unchanged over some period of time. Due to residual reactions, a small increase of viscosity may be observed.
3) 3rd state, cured, solid, elastic state after curing time according to ISO 4823;

A) transition from the mixer-suitable to the heavy-bodied to putty consistency through a condensation reaction of the SiOR groups and/or hydrosilylation reaction between alkynyl and SiH groups;
B) transition from the heavy-bodied to putty consistency to the cured state through cross-linking by a hydrosilylation reaction between alkenyl and SiH groups.

Figure 2:
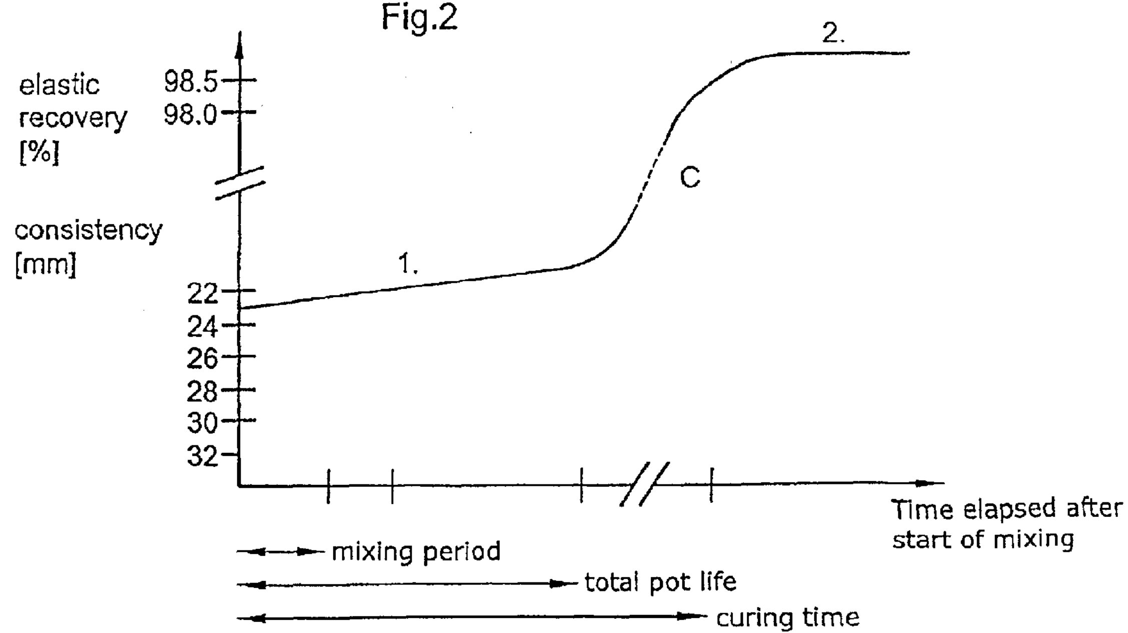

In contrast, FIG. 2 shows the corresponding kinetics for the change in consistency of a putty material of the prior art in an idealized form. Here, only two consistencies, which are relatively stable for some time, can be distinguished; they are linked by a single reaction step:

1) 1st state, non-mixer-suitable consistency during the total pot life according to ISO 4823;
2) 2nd state, cured, solid, elastic state after curing time according to ISO 4823;

C) transition from the first, non-mixer-suitable consistency to the cured state through cross-linking by a hydrosilylation reaction between alkenyl and SiH groups.

The invention also relates to methods for the preparation of impressions from objects from which impressions are to be made.

In the method according to the invention, an impression material is first prepared by mixing the components A and B. The impression material is first dispensed in a first state from a container through a mixer. During and after mixing, it undergoes transition to a second state in which the viscosity of the impression material is clearly increased, whereupon an impression is prepared from an object from which an impression is to be made. Thereafter, the impression material undergoes transition to a third, solid state in which an impression result is recorded, the second state being achieved by graded hydrosilylation reactions between alkynyl and alkenyl structural units with compounds containing Si—H groups and/or by graded addition reactions (between alkenyl and SiH groups) and condensation reactions (of SiOR groups with condensation catalysts).

Preferably, the consistency of the impression material in the first state at the beginning of mixing is >26 mm, more preferably >30 mm, according to ISO 4823. In this first state, the impression material is mixer-suitable. The consistency of the impression material in the second state is especially <35 mm, especially <30 mm (according to ISO 4823), the impression material being heavier-bodied (more viscous) than it is in the first state. The impression material preferably remains in this second state until the end of the presettable total pot life, at least for 15 s. Preferably, the third, solid state is an elastic state.

With the present invention, it is possible to prepare support materials based on addition-cross-linkable polymers, especially polydimethylsiloxanes, for the making of dental impressions which can be dispensed from the recently developed automatic mixing and dosing systems due to their mixer-suitable consistency.

This heavy-bodied to putty consistency is retained over a presettable period of time, especially over the pot life needed by the dentist.

Towards the end of the pot life, the impression material is introduced into the mouth. Now, the second reaction step starts, and the material cures completely. The cured product obtained has the mechanical properties of a cured dental impression material according to ISO 4823.

In this way, the requirements and advantages of a heavy-bodied to putty consistency support material are achieved while the mentioned drawbacks due to mixing and dosing errors and contamination are circumvented.

With the two-step curable mixer-suitable materials according to the invention, it is possible to dispense kneadable materials from automatic mixing and dosing systems. The increase in viscosity by the two-step reaction mechanism can be controlled in such a way that a multicomponent impression material which is mixer-suitable at first and can be dispensed from manual and automatic mixing and dosing systems quickly undergoes transition to a kneadable consistency during and after the mixing period (according to ISO 4823). This kneadable consistency is retained until the end of the total pot life of the impression material.

The mixer-suitable multicomponent impression material according to the invention can be prepared in such a way that a kneadable impression material exhibits the tack-free behavior of a classical putty material after dispensing from a manual or automatic mixing or dosing system. Tack-free processing and spreading of the impression material with the finger is possible. In the sandwich shaping technique, the user can dent the necessary hollow with the finger without sticking.

Further, with another embodiment of the mixer-suitable impression materials according to the invention, it is possible to prepare particularly advantageous alginate substitute materials for the making of temporary impressions. Here, the heavy decrease in consistency (increase in viscosity) due to the first reaction step of the two-step reaction mechanism after dispensing from a manual or automatic mixing and dosing system is utilized for obtaining particularly non-sag and heavy-bodied consistencies.

This alginate-like consistency is retained during the whole pot life of the impression material according to ISO 4823 and makes it possible for the user to spread the material with the finger on the teeth from which an impression is to be made with no material sticking to the fingers, prior to introducing the impression tray.

The described transition of the mixtures from a first state to a second state of higher viscosity and further to a third, solid state according to the invention is achieved, inter alia, by the following preferred embodiments:

In an embodiment according to the invention, e.g., on a polysiloxane basis, the increase in viscosity of the impression material to a heavy-bodied or putty consistency is achieved by linking mainly α-monoethynylpolysiloxanes to the polymethylhydrogensiloxane by hydrosilylation. A heavily branched structure is formed from the polymethylhydrogensiloxane chain by the "docking" therewith of the monoethynylpolysiloxanes, which structure can more vividly be described as a "porcupine polymer". In this way, polymers having a very high molecular weight are constructed, but which do not exhibit any cross-linking between each other.

An addition of dialkynylpolysiloxanes can additionally enlarge the molecular weight jump to a high extent.

Once the majority of the alkynylpolydimethylsiloxanes, which react first, have reacted, the second reaction step begins after a pot life which can be preset by inhibitors.

In this step, the dialkenylpolysiloxanes react with the remaining SiH groups of the "porcupine polymer" which has become highly branched in the first step. In the dental application in the patient's mouth, this second step results in the cross-linking and complete curing of the elastomeric dental impression material.

By selectively using inhibitors, the respective kinetics can be controlled in the first and second reaction steps in accordance with the respective requirements of practice.

Another embodiment of the invention uses dialkynylpolysiloxanes for the first reaction step. The reaction of the dialkynylpolysiloxanes with an excess of linear dihydrogenpolysiloxanes to yield long linear polymer chains of high molecular weight causes the desired viscosity jump, which is equivalent to the transition from the first state to the second state.

Once the majority of the alkynylpolysiloxanes, which react first, have reacted, the second reaction step begins. In this step, branched polysiloxanes having at least three vinyl groups react with the SiH groups of the dihydrogenpolysiloxanes, which are now terminal to the polymer.

In the dental application in the patient's mouth, this second step results in the cross-linking and complete curing of the elastomeric dental impression material.

An addition of tri- or polyhydrogensiloxanes can additionally enlarge the molecular weight jump to a high extent.

In another embodiment of the invention, an exactly defined concentration of a dialkynylpolysiloxane reacts with a polyhydrogensiloxane, preferably having a high molecular weight (from 1000 to 450,000 g/mol) in a first reaction step. Due to the linking together, polysiloxanes having a high molecular weight are quickly constructed. In the behavior of the impression material, this is manifested by a viscosity jump according to the invention.

After all the ethynylsiloxanes have reacted, in a second reaction step, the excess SiH groups react with the available dialkenylpolysiloxanes. In the dental application in the patient's mouth, this second step results in the cross-linking and complete curing of the elastomeric dental impression material.

In the last three embodiments mentioned above, the first reaction step is a hydrosilylation between the alkynyl group and the SiH group. In this reaction step, only a slight cross-linking is permitted since otherwise elastic fractions will build already during the pot life. The elastic fractions formed would result in compressions (endogenous strains) during the pot life in the preparation of the impressions, which would eventually lead to non-fitting dental prostheses.

In another embodiment of the invention, an α,ω-dihydroxy- or dialkoxypolysiloxane reacts with a titanic acid ortho ester, such as titanium(IV) tetrapropylate, in a first reaction step. Due to the condensation reaction occurring, polysiloxanes having a high molecular weight are constructed relatively quickly. In the behavior of the impression material, this is manifested by a viscosity jump.

After the hydroxy- or alkoxysiloxanes have reacted, in a second reaction step, organohydrogensiloxanes react with the available dialkenylpolysiloxanes in a platinum-catalyzed addition reaction. In the dental application in the patient's mouth, this second step results in the cross-linking and complete curing of the elastomeric dental impression material. Of course, the mechanism described can also proceed in reversed order, i.e., first the addition and then the condensation, depending on the type and concentration of the catalysts and the type and concentration of the inhibitors employed.

In another embodiment of the invention, in a first reaction step, the alkynyl group of a dialkynylpolysiloxane reacts with a polyhydrogensiloxane, and an α,ω-dihydroxy- or dialkoxysilane reacts with a titanic acid ortho ester. Due to the alkyne addition reaction and the condensation reaction occurring, polysiloxanes having a high molecular weight are quickly constructed. In the Theological behavior of the impression material, this is manifested by a viscosity jump.

After the alkynyl groups and the hydroxy or alkoxy groups have reacted, in a further reaction step, organohydrogenpolysiloxanes react with the available dialkenylpolysiloxanes in a platinum-catalyzed addition reaction. In the dental application in the patient's mouth, this step results in the cross-linking and complete curing of the elastomeric dental impression material. Of course, the mechanism described can also proceed in reversed order with respect to the condensation reaction and the addition reaction with SiH and alkenyl, i.e., first the addition and then the condensation, depending on the type and concentration of the catalysts and the type and concentration of the inhibitors.

In a further embodiment according to the invention, e.g., on the basis of polysiloxanes, the increase in viscosity of the impression material to a heavy-bodied or putty consistency is achieved by mainly linking α-monohydroxypolysiloxanes, e.g., to the titanium alkoxide, by condensation. A branched structure is formed from the titanium alkoxide by the "docking" therewith of the monohydroxypolysiloxanes, which structure may more vividly and plastically be referred to as a "porcupine polymer". In this way, polymers having a very high molecular weight are constructed, but which do not exhibit any cross-linking between each other. An addition of dihydroxypolysiloxane can additionally enlarge the molecular weight jump to a high extent.

Once the majority of the hydroxypolydimethylsiloxanes, which react first, have reacted, the second reaction step begins after a pot life which can be preset by inhibitors.

In this step, the dialkenylpolysiloxanes react with the available SiH groups of the organohydrogenpolysiloxane. In the dental application in the patient's mouth, this second step results in the cross-linking and complete curing of the elastomeric dental impression material.

By selectively using inhibitors, the respective kinetics can be controlled in the first and second reaction steps in accordance with the respective requirements of practice.

If α-hydroxy-ω-vinylpolysiloxanes are employed instead of the monohydroxysiloxanes, the porcupine polymers formed can be incorporated in the polymer matrix in the second reaction step by hydrosilylation through the remaining freely available Si-vinyl groups.

EXAMPLES

Example 1

Kinetic examinations on model systems relating to the reaction rate of ethynyl and vinyl groups in the platinum-catalyzed hydrosilylation (according to the invention).

Design and performance of the kinetic experiments: GC analysis: 30 m FS capillary column, film 1.0 μm, covered with 100% polydimethylsiloxane (Econo-Cap capillary EC-1 of Alltech GmbH). Column preliminary pressure 0.35 bar of $H_2$. Temperature split injection and FID at 250° C.

Catalytic batch: Pt catalyst is charged first, addition of pentamethyldisiloxane, stirring at 33° C. for 20 to 40 min. Injecting the unsaturated substrate. Sampling of 1 ml samples at the respective reaction time to be examined, dilution with 4 ml of a TMEDA solution (containing 0.5 mmol of TMEDA/4 ml) for quenching the reaction. Injecting 1 μl of this solution for GC analysis.

a) Kinetic Examination of the Hydrosilylation of Vinyltrimethylsilane

According to the method described above, 0.5 g (5 mmol) of vinyltrimethylsilane is reacted with 1.5 g of pentamethyldisiloxane (10 mmol) in 5.2 g of trimethylsilyl-end-stopped polydimethylsiloxane ($MD_{14}M$) as a solvent in the presence of 0.1 mg of platinum catalyst (in the form of divinyltetramethyldisiloxane-platinum complex, 1% in xylene), which corresponds to a pure platinum content of 50 ppm. The course of the reaction cannot be followed by GC analysis since the vinyltrimethylsilane has completely reacted after about 30 s with superheating.

b) Kinetic Examination of the Hydrosilylation of Ethynyltrimethylsilane

According to the method described above, 0.5 g (5 mmol) of ethynyltrimethylsilane is reacted with 3.0 g (20 mmol) of pentamethyldisiloxane in 5.2 g of trimethylsilyl-end-stopped polydimethylsiloxane ($MD_{14}M$) as a solvent in the presence of 0.1 mg of platinum catalyst (employed in the form of divinyltetramethyldisiloxane-platinum complex, 1% in xylene), which corresponds to a pure platinum content of 50 ppm. The reaction mixture is examined by GC analysis at different times. Monoaddition and diaddition products are formed. After 1000 s, ethynyltrimethylsilane has been completely consumed to form 80% monoaddition product and 20% diaddition product. After 3 days at 35° C., the diaddition product has been formed at 98%.

c) Kinetic Examination of the Hydrosilylation of a Mixture of Ethynyltrimethylsilane and Vinyltrimethylsilane According to the method described above, a mixture of 0.3 g of vinyltrimethylsilane and 0.3 g of ethynyltrimethylsilane is reacted with 1.5 g of pentamethyldisiloxane in 5.2 g of trimethylsilyl-end-stopped polydimethylsiloxane ($MD_{14}M$) as a solvent in the presence of 0.1 mg of platinum catalyst (employed in the form of divinyltetramethyldisiloxane-platinum complex, 1% in xylene), which corresponds to a pure platinum content of 50 ppm. In this reaction, ethynyltrimethylsilane is consumed more quickly than vinyltrimethylsilane. After 600 s, the whole ethynyltrimethylsilane has been consumed to form 80% monoaddition product and 20% diaddition product. In contrast, the partial reaction between vinyltrimethylsilane and pentamethyldisiloxane is clearly decelerated as compared with Example 1a). After 1500 s, the whole vinyltrimethylsilane has been consumed.

Discussion of the Results of the Kinetic Examinations from Examples 1a) to c)

In the individual experiment, the hydrosilylation of ethynyltrimethylsilane proceeds more slowly than the hydrosilylation of vinyltrimethylsilane (Examples 1a and 1b).

When a mixture of ethynyltrimethylsilane and vinyltrimethylsilane is employed for hydrosilylation (Example 1c), ethynyltrimethylsilane reacts preferably at first. This is due to the fact that ethynyltrimethylsilane coordinates to the platinum more firmly or more quickly as compared to vinyltrimethylsilane. A notable reaction of vinyltrimethylsilane occurs only when the ethynyltrimethylsilane has been consumed almost completely.

According to the invention, this two-step course of the reaction can be utilized for the preparation of two-step curable silicone materials by using the hydrosilylation of ethynyl groups for the construction of high molecular weights or viscosities and using the time-shifted hydrosilylation of vinyl groups for cross-linking.

Example 2

Behavior of ethynyltrimethylsilane as a model compound in an addition-cross-linkable silicone material (according to the invention).

a) In a mixer, 2 parts of ethynyltrimethylsilane is dissolved with 38 parts of a vinyl-end-stopped polydimethylsiloxane having a viscosity of 1000 mPa·s and a vinyl content of 0.13 mmol/g to obtain a colorless clear 5% solution.

b) In a mixer, 3 parts of the mixture prepared under a) is homogeneously compounded into 100 parts of component 2 (SiH component) of an uninhibited medium-bodied impression material.

c) 50 parts of component 2 prepared under b) is homogeneously mixed with 50 parts of component 1 (Pt component) of a medium-bodied impression material from a dual-chamber cartridge through a static mixer to obtain a medium-bodied impression material (according to DIN EN 24823) having a total pot life of one minute and a curing end of 2.5 minutes.

Example 2 demonstrates that Si-ethynyl groups in an addition-cross-linkable silicone material have no strongly inhibiting influence on the curing behavior. The concentration of ethynyl, being 1.5 mmol/100 g, was selected as would be necessary for adjusting the desired increase in molecular weight when monoethynylpolydimethylsiloxane was used. The transition from the medium-bodied to putty consistencies is concluded after one minute as judged by this model reaction.

Example 3

Model experiments relating to two-step curable addition- and condensation-cross-linkable mixer-suitable silicone materials (according to the invention).

a) In a vacuum mixer, 196 parts of an α,ω-divinylpolydimethylsiloxane having a viscosity of 1000 mpa·s (at 23° C.), a molecular weight of about 15,000 g/mol and a vinyl content of 0.13 mmol/g was homogeneously mixed with 2.5 parts of a platinum-siloxane complex dissolved in divinylpolydimethylsiloxane having a pure platinum content of 1% and 1.5 parts of titanium(IV) tetrapropylate to obtain a very light-bodied mixture having a viscosity of about 800 mPa·s (at 23° C.), which represents component 1 of the addition- and condensation-cross-linkable silicone material curable in two steps according to the invention.

b) In a vacuum mixer, 113 parts of a polymethylhydrogensiloxane having a viscosity of 200 mPa·s (at 23° C.), a molecular weight of about 7000 g/mol and an SiH content of 1.8 mmol/g was homogeneously mixed with 83 parts of an α,ω-dihydroxypolydimethyl-siloxane having a viscosity of 2000 mPa·s (at 23° C.), 0.34 part of 1,2-divinyltetramethyldisiloxane and 3 parts of α,ω-divinylpolydimethyl-siloxane having a viscosity of 1000 mPa·s (at 23° C.) to obtain a very light-bodied mixture having a viscosity of 500 mPa·s (at 23° C.), which represents component 2 of the addition- and condensation-cross-linkable silicone material curable in two steps according to the invention.

c) On a mixing block, 3 parts of component 1 from Example 3a) and 1 part of component 2 from Example 3b) are mixed within 30 s using a mixing spatula. The material undergoes an increase in viscosity within a short period of time. Immediately after the mixing, the viscosity of the mixture is 20,000 mPa·s. This high viscosity is retained over a period of about five minutes. Towards the end of this pot life, the second reaction step starts, and the material cures at room temperature within 12 minutes.

This Example illustrates that it is possible to form a two-step reaction mechanism with the composition according to the invention, whereby a mixer-suitable material, which is very light-bodied at first, undergoes a transition, through a viscosity jump, to a heavier-bodied material which, in a second reaction step, cross-links to form an elastomeric solid after a reasonable pot life.

According to the invention, this behavior can be utilized for the preparation of heavy-bodied to kneadable impression materials which can be easily dispensed from commercially available mixing and dosing devices. Surprisingly, it is found in Example 3c according to the invention that the addition of water is not required for the reaction of the condensation cross-linker with the polymers having SiOH groups. In contrast, even a slight addition of water prevents the occurrence of a viscosity jump. In contrast, with the systems for (dental) impression materials known from the literature, the addition of water is required ("Silicone: Chemie und Technologie", Vulkan Verlag Essen 1989, p. 55; W. Noll, "Chemie und Technologie der Silicone", 2nd ed., Verlag Chemie 1968, page 340).

The preparation of corresponding two-step curable impression materials is described in Examples 4 and 5.

Example 4

Formulations of two-step curable addition-cross-linkable and condensation-cross-linkable mixer-suitable silicone materials (according to the invention).

a) In a kneader, 67 parts of silica flour, 1 part of highly dispersed silicic acid having a BET surface area of 200 $m^2/g$ and 2 parts of a molecular sieve are homogeneously mixed with 8 parts of mineral oil having a viscosity of 200 mPa·s, 0.5 part of a Pt-siloxane complex dissolved in divinylpolysiloxane having a pure platinum content of 1.0%, 21.0 parts of a vinyl-end-stopped polydimethylsiloxane having a viscosity of 1000 mPa·s (at 23° C.) and 0.5 part of titanium(IV) tetrapropylate.

b) In a kneader, 67 parts of silica flour, 1 part of highly dispersed hydrophobized silicic acid having a BET surface area of 200 $m^2/g$ and 2 parts of a molecular sieve are homogeneously mixed with 8 parts of mineral oil having a viscosity of 200 mPa·s (at 23° C.), 5 parts of a polymethylhydrogensiloxane having a molecular weight of about 7000 g/mol and an SiH content of 1.8 mmol/g and 7 parts of a divinylpolydimethylsiloxane having a viscosity of 1000 mPa·s (23° C.) and a vinyl content of 0.13 mmol/g, and 10 parts of α,ω-dihydroxypolydimethylsiloxane having a viscosity of 2000 mPa·s and an SiOH content of 0.1 mmol/g to obtain a medium-bodied paste, which represents component 2 (SiH component) of the silicone material curable in two steps according to the invention.

c) From a dual-chamber cartridge, 50 parts of component 1 from Example 4a) and 50 parts of component 2 from Example 4b) are homogeneously mixed through a static mixer using a dosing pistol. Since the impression material, in the form of its separated components, has a medium-bodied consistency, it can be easily dispensed through known electrically, pneumatically or manually operated mixing and dosing systems (Mixpac, EP 0 615 787 A1). During and after the end of mixing, the first reaction step starts. The mixture is dispensed after the mixing, so that the first reaction step proceeds outside the mixture for the major part thereof.

Within a short period of time, the material undergoes an increase in viscosity and undergoes transition to a putty consistency according to ISO 4823 preimpression material. This putty consistency is retained over some period of time. Towards the end of the pot life, the impression material is introduced into the patient's mouth. Now, the second reaction step starts, and the material cures completely. The cured product obtained has the mechanical properties of a putty material according to ISO 4823.

Example 5

Formulations of two-step curable addition-cross-linkable and condensation-cross-linkable mixer-suitable silicone materials (according to the invention).

a) In a kneader, 67 parts of silica flour, 1 part of highly dispersed silicic acid having a BET surface area of 200 $m^2/g$ and 2 parts of a molecular sieve are homogeneously mixed with 8 parts of mineral oil having a viscosity of 200 mPa·s, 6 parts of $\alpha,\omega$-diethynylpolydimethylsiloxane having a viscosity of 1000 mPa·s, a molecular weight of about 15,000 g/mol and an ethynyl content of about 0.13 mmol/g and 15 parts of $\alpha,\omega$-divinylpolydimethylsiloxane having a viscosity of 1000 mPa·s, a molecular weight of about 15,000 g/mol and a vinyl content of 0.13 mmol/g, 0.5 part of a platinum-siloxane complex dissolved in vinylsiloxane having a pure platinum content of 1% and 0.5 part of titanium(IV) tetrapropylate to obtain a medium-bodied paste, which represents component 1 of the silicone material curable in two steps according to the invention.

b) In a kneader, 67 parts of silica flour, 1 part of highly dispersed hydrophobized silicic acid having a BET surface area of 200 $m^2/g$ and 2 parts of a molecular sieve are homogeneously mixed with 8 parts of mineral oil having a viscosity of 200 mPa·s, 6 parts of polymethylhydrogensiloxane having a molecular weight of 7000 g/mol and an SiH content of 1.8 mmol/g and 6 parts of an $\alpha,\omega$-divinylpolydimethylsiloxane having a viscosity of 1000 mPa·s, a molecular weight of about 15,000 g/mol and a vinyl content of 0.13 mmol/g, and 10 parts of an $\alpha,\omega$-dihydroxypolydimethylsiloxane having a viscosity of 2000 mPa·s (at 23° C.) to obtain a medium-bodied paste, which represents component 2 of the addition-cross-linkable and condensation-cross-linkable silicone material curable in two steps according to the invention.

c) From a dual-chamber cartridge, 50 parts of component 1 from Example 5a) and 50 parts of component 2 from Example 5b) are homogeneously mixed through a static mixer using a dosing pistol. Since the impression material, in the form of its separated components, has a medium-bodied consistency, it can be easily dispensed through known electrically, pneumatically or manually operated mixing and dosing systems (Mixpac, EP 0 615 787 A1). After the mixing, the first reaction step starts. The mixture is dispensed after the mixing, so that the first reaction step proceeds outside the mixture for the major part thereof. Within a short period of time, the material undergoes an increase in viscosity and undergoes transition to a putty consistency according to ISO 4823. This putty consistency is retained over some period of time. Towards the end of the pot life, the impression material is introduced into the patient's mouth. Now, the second reaction step starts, and the material cures completely. The cured product obtained has the mechanical properties of a putty material according to ISO 4823.

The results are discussed in connection with Example 6.

Example 6

Formulations of two-step curable addition-cross-linkable and condensation-cross-linkable mixer-suitable silicone materials (according to the invention).

a) In a kneader, 47 parts of silica flour and 15 parts of highly dispersed hydrophobized silicic acid having a BET surface area of 200 $m^2/g$ are homogeneously mixed with 18 parts of mineral oil having a viscosity of 200 mPa·s, 15 parts of vaseline, 3 parts of a platinum-siloxane complex dissolved in vinylsiloxane having a pure platinum content of 1% and 2 parts of titanium(IV) tetrabutylate to obtain a medium-bodied paste, which represents component 1 of the silicone material curable in two steps according to the invention.

b) In a kneader, 66 parts of silica flour and 2.5 parts of highly dispersed hydrophobized silicic acid having a BET surface area of 200 $m^2/g$ are homogeneously mixed with 7 parts of polymethylhydrogensiloxane having a molecular weight of 7000 g/mol and an SiH content of 1.8 mmol/g and 17 parts of an $\alpha,\omega$-divinylpolydimethylsiloxane mixture having a viscosity of 1200 mPa·s and a vinyl content of 0.13 mmol/g, 4 parts of an $\alpha$-hydroxy-$\omega$-vinylpolydimethylsiloxane having a viscosity of 5000 mPa·s and 2 parts of an $\alpha,\omega$-dihydroxypolydimethylsiloxane having a viscosity of 5000 mPa·s (at 23° C.) to obtain a medium-bodied paste, which represents component 2 of the addition-cross-linkable and condensation-cross-linkable silicone material curable in two steps according to the invention.

c) From a dual-chamber cartridge, 1 part of component 1 from Example 6 a) and 5 parts of component 2 from Example 6b) are homogeneously mixed through a static mixer using a dosing pistol. Since the impression material, in the form of its separated components, has a medium-bodied consistency, it can be easily dispensed from cartridges and tubular film bags through known electrically (Espe, Pentamix, EP 0 492 413 D1; DMG, Mixstar, DE 10013812 A1, Mixpac EP 0 956 908 A1) pneumatically or manually operated mixing and dosing systems (Mixpac, EP 0 615 787 A1). During and after mixing, the first reaction step starts. The mixture is dispensed after the mixing, so that the first reaction step proceeds outside the mixture for the major part thereof. Within a short period of time, the material undergoes an increase in viscosity and undergoes transition to a putty consistency according to ISO 4823. This putty consistency is retained over some period of time. Towards the end of the pot life, the impression material is introduced into the patient's mouth. Now, the second reaction step starts, and the material cures completely. The cured product obtained has the mechanical properties of a putty material according to ISO 4823:

| | |
|---|---|
| deformation under pressure: | 2.5% |

-continued

| | |
|---|---|
| elastic recovery: | 99.4% |
| linear dimensional change: | −0.2% |
| Shore A hardness (DIN 53505): | 70 |
| tensile strength at break (DIN 53504): | 160 N/cm$^2$ |

Discussion of Examples 5 and 6

In the combination according to the invention of the addition cross-linking of alkenyl with SiH and the condensation reaction of SiOR with metal alkoxides with or without the addition of alkynyl with SiH as described in Examples 5c and 6c, it is found that the addition reaction and the condensation reaction proceed practically independently of each other and have no mutual negative influence on each other. Surprisingly, the reaction between SiOH and SiH in the presence of platinum with evolution of hydrogen (formation of gas bubbles) to be expected by one skilled in the art and known from the literature ("Silicone: Chemie und Technologie", Vulkan Verlag Essen 1989, p. 55; W. Noll, "Chemie und Technologie der Silicone", 2nd ed., Verlag Chemie 1968, page 340) is not observed.

The above-mentioned combination according to the invention shows a linear dimensional change according to ISO 4823 which is on the same order as with the commercially available addition-cross-linkable silicones. The linear dimensional change is between −0.1% and −0.3% while the commercially available condensation-cross-linkable silicones have values of between −0.6% and −1.5% (J. Wirz, "Abformung in der zahnärztlichen Praxis, Gustav Fischer Verlag 1993, p. 56, 57; Dr. Wöstmann, "Zum derzeitigen Stand der Abformung in der Zahnheilkunde", Habilitationsschrift, University of Münster, Germany, p. 18ff). Example 6c according to the invention exhibits a linear dimensional change of 0.20%.

The separated components of Examples 5a and 6a, which comprise a cross-linking agent/catalyst combination consisting of metal alkoxides, especially titanates and hydrosilylation catalysts, especially Pt complexes, show a high storage stability in suitable primary packages both at room temperature and in thermal stress test conditions at 60° C. In this way, the minimum storage time of a commercial product of 6 months as required in practice is met.

In the composition according to the invention, the condensation cross-linking agent contained in the separated components of Examples 5a and 6a (metal alkoxides, especially titanates) has a high storage stability sufficient for practical conditions in a suitable primary package, such as aluminum-coated tubular film bags or water-vapor-impermeable plastic cartridges. This means that the activity of the condensation-cross-linking metal alkoxides, especially titanates, results in a sufficient increase in molecular weight and the associated viscosity jump despite of the potential presence of water traces. In this way, the minimum storage time of a commercial product of 6 months as required in practice is met.

Surprisingly, the separated components of Examples 5b and 6b in which polymers having SiH and SiOH groups coexist do not show any reaction to make Si—O—Si linkages with cleavage of hydrogen either at room temperature or under thermal stress conditions at 60° C., i.e., an increase in viscosity of the above mentioned separated components or expansion of the primary package by hydrogen gas could not be observed.

Example 7

Comparative Example

Commercially Available Kneadable Preimpression Material (Not According to the Invention)

The commercially available putty materials Panasil Putty (Kettenbach #7399) and Provil novo putty fast set (Heraeus-Kulzer, lot No. 090554/090439), respectively separated into components 1 and 2, are filled into dual-chamber cartridges (EP 0 723 807 A2) or tubular film bags (cf. EP-A-0 541 972, PCT/EP 98/01993).

Due to the high discharging forces, dispensing of the above mentioned putty materials from the dual-chamber cartridge with a dosing pistol (Mixpac) through a static mixer (Mixpac MA 7,5-12-D) and filling of a commercially available impression tray is not possible within the total pot life according to ISO 4823.

Due to the high discharging and frictional forces, dispensing of the above mentioned putty materials from a tubular film bag using an electrically operated mixing and dosing device (Mixpac Type BD 400-230-0000, Serial No. Vorserie 00029, EP 0 956 908 A1; Espe, Pentamix 2; EP-A-0 492 413) through a dynamic mixer (EP-A-0 492 412) and filling of a commercially available impression tray is not possible within the total pot life.

This Example illustrates that a commercially available putty material cannot be processed with automatic mixing and dosing systems, which is in contrast to the impression material according to the invention.

Example 8

Comparative Example

Commercially Available Putty Cartridge Material (Not According to the Invention)

The commercially available product Reprosil Quixx Putty of Dentsply Caulk is examined; on its package slip, the following statement is made:

"After dispensing from a dual-chamber cartridge using a static mixer, it undergoes a transition from an immediate mixing viscosity through a tray viscosity to a putty viscosity one minute after the start of mixing." The ideal putty viscosity is achieved after from 1 minute and 15 seconds to 1 minute and 30 seconds. During this time window, the material behaves like a traditional putty material.

The above-mentioned commercial product is an addition-cross-linkable silicone known from the prior art, i.e., siloxane polymers with vinyl groups react with hydrogenpolysiloxanes, which results in cross-linking.

This means that the viscosity continuously increases due to the proceeding cross-linking without retaining a putty-like consistency (in contrast to the two-step reaction mechanism according to the invention).

This results in the following consequences:

The time window in which the putty consistency is retained is extremely short and therefore difficult to calculate for the user (dentist) (e.g., influence of external temperature on kinetics).

The short time window of 15 seconds involves the following risks:

When the predetermined time of 1 minute and 15 seconds is not yet reached, e.g., after one minute, the mixing consistency is not yet sufficiently high so that only a low pressure is built by the impression material when the impression is made.

When the predetermined time of 1 minute and 30 seconds is exceeded, the cross-linking is already very much advanced so that the elastic properties are predominant over the plastic properties and thus the risk of endogenous strains and compressions is extremely high when the impression is made.

This necessarily results in unacceptable impression results.

In addition, in the defined time window of from one minute and 15 seconds to one minute and 30 seconds, the commercial product Reprosil Quixx Putty does not show the kneadable and non-tacky properties familiar from the traditional putty when handled between the fingers, but it behaves like a medium-bodied impression material which cures according to the one-step hydrosilylation mechanism and exists in a transition from the plastic to the elastic state. It gives a tacky feel between the fingers.

Examples 3 to 5 demonstrate that it is possible, using the silicone materials having the composition according to the invention, to provide a material which, in the form of its separated components, has a light- to heavy-bodied consistency, can be easily dispensed by known electrically, pneumatically or manually operated mixing and dosing systems and undergoes an increase in viscosity within a short period of time (i.e., the consistency of the impression material after mixing according to ISO 4823 undergoes a transition from a light-bodied consistency (type 3) or medium-bodied consistency (type 2) to a heavy-bodied consistency (type 1) or putty consistency (type 0), or from a heavy-bodied consistency (type 1) to a putty consistency (type 0)).

The silicone material according to the invention combines the advantages of putty cartridge materials, such as suitability for automatic mixing and dosing, with the advantages of the classical kneadable support materials, such as building of force pressure during the making of the impression, non-tackiness in the putty-like state, and a reasonable total pot life, due to a two-step reaction mechanism and thus avoids the above mentioned drawbacks of the support materials of the prior art.

Example 9

In order to define the concept of "mixer-suitable" more precisely, the dischargeability of prior art materials was determined. Dischargeability was determined for 7 materials, each with an automatic and a manual mixing and dosing system. The results are summarized in Table 1.

TABLE 1

Mixer-suitability of prior art materials

| Type of material according to ISO 4823 | Consistency of mixture according to ISO 4823 | Dischargeability from automatic mixing and dosing systems[1)] | Dischargeability from manual mixing and dosing systems[2)] |
|---|---|---|---|
| putty[3)] | 22 mm | not dischargeable | not dischargeable |
| putty[4)] | 24 mm | not dischargeable | not dischargeable |
| heavy-bodied[5)] | 26 mm | very hardly dischargeable | not dischargeable |
| heavy-bodied[6)] | 28 mm | hardly dischargeable | not dischargeable |
| heavy-bodied[7)] | 30 mm | acceptable | very hardly dischargeable |
| heavy-bodied[8)] | 32 mm | acceptable | hardly dischargeable |
| heavy-bodied[9)] | 34 mm | acceptable | acceptable |

TABLE 1-continued

Mixer-suitability of prior art materials

| Type of material according to ISO 4823 | Consistency of mixture according to ISO 4823 | Dischargeability from automatic mixing and dosing systems[1)] | Dischargeability from manual mixing and dosing systems[2)] |
|---|---|---|---|

[1)]Pentamix 1, Espe, dynamic mixer, cartridge with tubular film bag; Pentamix II, Espe, dynamic mixer, cartridge with tubular film bag; Mixstar, DMG, dynamic mixer, cartridge with tubular film bag; BDG 400 Bulk Dispenser (prototype), Mixpac, dynamic mixer, cartridge CDB 400-01-V02;

[2)]System S 50, Mixpac, static mixer MB 7,5-11-D, cartridge CS 050-01-09, dispenser DS 50-01-00; System 50, Mixpac, static mixer MA 7,5-12-D, cartridge CD 051-01-09, dispenser DM 51-KE-1 I, TZAH, static mixer 190-712 D, cartridge BS-101-01, dispensing pistol DK-104;

[3)]Panasil Putty regular set, Kettenbach;

[4)]Panasil Putty soft, Kettenbach;

[5)]experimental product Panasil Plus heavy, Kettenbach;

[6)]experimental product Panasil Plus heavy, Kettenbach;

[7)]experimental product Panasil Plus heavy, Kettenbach;

[8)]Panasil Tray fast set, Kettenbach;

[9)]Kettosil, Kettenbach.

[10)]Aquasil soft putty, DeTrey Dentsply, Pentamix II and BDG 400. (An unacceptable increase of temperature was detected during the dispensing. The dispensed volume quantity was only 17 ml after 1 min and was thus far too small).

Example 10

Table 2 sets forth the dispensed quantity of different commercial products as compared to the impression material according to the invention, e.g., according to Example 6c), with different dispensing devices.

Further, the mixture consistencies and the properties of "kneadability" and "tackiness" are evaluated.

From Table 2, it can be seen that only Example 6c) according to the invention has an extremely low mixture consistency of 22 mm, is kneadable and non-tacky, but nevertheless can be dispensed from commercially available dispensing devices in a quantity suitable for practice. The dispensing of the material having a consistency of only 22 mm is possible according to the invention because this consistency is reached in the mixer only by a continuous increase of viscosity. Therefore, in the mixer, only that part of the material which is about to be dispensed has such a relatively high viscosity. This relatively high viscosity then no longer affects dispensability. In contrast, a prior art material which is fed to a mixer already with a consistency of 22 mm is not dispensable as shown in Example 9.

TABLE 2

| Supplier: product and lot | dispensed quantity in g/min; dispensing device: Mixstar[a)] | Penta I[b)] | Penta II[c)] | Consistency[1)] of the mixture in mm | kneadable[2)] | tacky[3)] |
|---|---|---|---|---|---|---|
| Espe: Permadyne Penta H, Kat 551, Base 270, Pentamatic | 48.6 | 57 | 82.4 | 32 | no | yes |
| Espe: Impregum Penta, Kat N80, Base E30, Pentamatic | 47.8 | 56.4 | 82.6 | 35 | no | yes |
| Espe: Dimension Penta H, Kat 459, Base 094 | 69.6 | 81 | 121.6 | 28 | no | yes |
| Dentsply: Aquasil heavy body Kat 000327, Base 0003000367 | 57.6 | 68 | 93.6 | 29 | no | yes |
| Coltene: President heavy body Kat 07, Base 11 | 58.2 | 69.4 | 92.2 | 29 | no | yes |
| Kettenbach: Panasil Tray fast Kat 00021, Base 00021 | 63 | 75.6 | 118.6 | 32 | no | yes |
| Example 6c) according to the invention | 54 | 67 | 103 | 22 | yes | no |

[a)]Ser. NO.: 99–678,
[b)]Ser. NO.: 535617, Espe;
[c)]Ser. NO.: 5106647, Espe
[1)]Determination according to ISO 4823;
[2)]the material can be kneaded between the fingers immediately following machine-operated dispensing;
[3)]i.e., it is not possible to knead the material immediately following the mixing process due to its tackiness.

What is claimed is:

1. A multi-component system for making impressions which contains (a) at least one compound having at least two alkenyl groups;

(b) at least one organohydrogenpolysiloxane;

(c) at least one hydrosilylation catalyst;

characterized by containing one or both of components ($d_1$) and ($d_2$), wherein ($d_1$) is

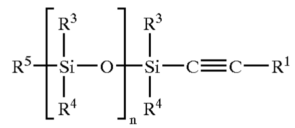

wherein n=7 to 6000, $R^1$=alkyl, aryl, arylalkyl, halogen-substituted alkyl or aryl groups, cyanoalkyl, cycloalkyl, —H, alkoxy, acyl and combinations thereof;

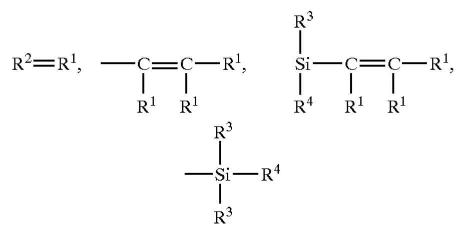

$R^3$=halogen, aryl, alkylaryl, H, halogen-substituted alkyl and aryl groups, alkyl, or combinations thereof;

$R^4$=$R^3$, or $R^4$ is different from $R^3$, wherein $R^4$ is alkyl, methyl, or combinations thereof; and $R^5$=H, alkyl, aryl, alkylaryl, halogen, halogen-substituted alkyl and aryl groups, —OR, aminoalkyl, epoxy, cyanoalkyl, cycloalkyl, methacrylate, acrylate, mercaptoalkyl, carboxylate, carboxyalkyl or succinic anhydride, and compound ($d_2$) is

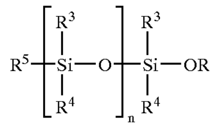

wherein n=7 to 6000,

R=H, alkyl, alkoxyalkyl or

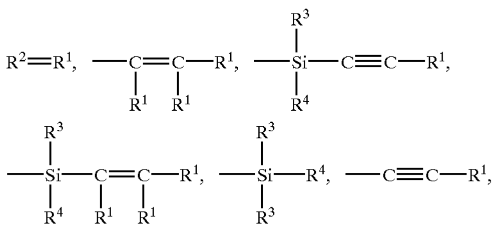

$R^1$=alkyl, aryl, arylalkyl, halogen-substituted alkyl or aryl groups, cyanoalkyl, cycloalkyl, —H, alkoxy, acyl, or combinations thereof;

$R^3$=alkenyl, alkynyl, halogen, aryl, alkylaryl, H, halogen-substituted alkyl, or aryl groups, alkyl, or combinations thereof;

$R^4$=$R^3$, or $R^4$ is alkyl, methyl, alkynyl, ethynyl, or combinations thereof; and $R^5$=—C≡C—$R^1$, H, alkyl, aryl, alkylaryl,

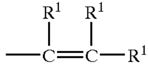

halogen, halogen-substituted alkyl and aryl groups, aminoalkyl, epoxy, cyanoalkyl, cycloalkyl, alkylhydroxyl, methacrylate, acrylate, mercaptoalkyl, carboxylate, carboxyalkyl or succinic anhydride; and when a compound ($d_2$) having an SiOR structural unit is contained, (e) at least one condensation catalyst or condensation cross-linking agent.

2. A multi-component system for making impressions according to claim 1 comprising at least two components A and B, characterized in that component A contains (a) at least one compound having at least two alkenyl groups; and (b) at least one organohydrogenpolysiloxane; and ($d_1$) at least one polymeric compound having at least one alkynyl group or ($d_2$) the at least one compound having an Si—OR structural unit, wherein R=H, alkyl, alkoxyalkyl or acyl;

and component B contains (c) at least one hydrosilylation catalyst; and when a compound ($d_2$) having an Si—OR structural unit is contained, component A, component B, or each of components A and B contains (e) at least one condensation catalyst or condensation cross-linking agent.

3. A multi-component system for making impressions according to claim 1 comprising at least two components A and B, characterized in that component A contains (a) the at least one compound having at least two alkenyl groups; and (b) the at least one organohydrogenpolysiloxane; and component B contains (c) the at least one hydrosilylation catalyst; and ($d_2$) the at least one compound having an Si—OR structural unit, wherein R=H, alkyl, alkoxyalkyl or acyl;

and either component A or B contains (e) the at least one condensation catalyst or condensation cross-linking agent.

4. A multi-component system for making impressions according to claim 1, characterized in that the alkenyl compound (a) is

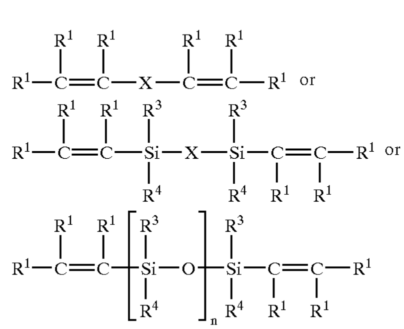

wherein n=0 to 6000; or a silane dendrimer having terminal alkenyl groups; wherein $R^1$=alkyl, aryl, arylalkyl, halogen-substituted alkyl and aryl groups, cyanoalkyl, cycloalkyl, cycloalkenyl, —H, —OH, alkoxy, acyl and combinations thereof;

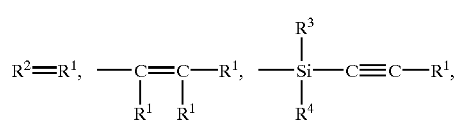

-continued

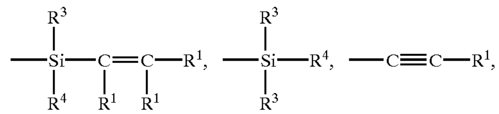

$R^3$=alkenyl, alkynyl, halogen, aryl, alkylaryl, H, halogen-substituted alkyl and aryl groups, alkyl, alkoxy and hydroxy, and combinations thereof;

$R^4$=$R^3$, or $R^4$ is different from $R^3$, wherein $R^4$ is, in particular, alkoxy, hydroxy, alkyl, methyl, alkynyl, ethynyl, or combinations thereof; and X=polysiloxane, oligosilicic acid esters, polysilicic acid esters, polyethers, polymeric hydrocarbons, polyesters and copolymers of the above mentioned compounds.

5. A multi-component system for making impressions according to claim 1, characterized in that the organohydrogenpolysiloxanes (b) are polyalkyl-, polyaryl- and polyalkylaryl-, polyhaloalkyl-, polyhaloaryl- or polyhaloalkylarylsiloxanes, which are present in the form of oligomers or polymers in a linear, branched or cyclic form or as a QM resin and have at least one Si—H bond.

6. A multi-component system for making impressions according to claim 1, characterized in that the condensation catalysts and the condensation cross-linking agents (e) are aluminum alkoxides, antimony alkoxides, barium alkoxides, boron alkoxides, calcium alkoxides, cerium alkoxides, erbium alkoxides, silicon alkoxides, gallium alkoxides, germanium alkoxides, hafnium alkoxides, indium alkoxides, iron alkoxides, lanthanum alkoxides, magnesium alkoxides, neodymium alkoxides, samarium alkoxides, strontium alkoxides, tantalum alkoxides, titanium alkoxides, tin alkoxides, vanadium alkoxide oxides, yttrium alkoxides, zinc alkoxides, zirconium alkoxides, titanium or zirconium compounds, titanium, zirconium and hafnium alkoxides, and double metal alkoxides, chelates and oligo- and polycondensates of the above alkoxides, dialkyltin diacetate, tin(II) octoate, dialkyltin diacylate or dialkyltin oxide.

7. A multi-component system for making impressions according to claim 1, characterized in that the hydrosilylation catalysts (c) are transition metals of the 8th auxiliary group, or platinum, palladium and rhodium or their salts, complexes and colloids, or platinum complexes and salts of hexachioroplatinic acid.

8. A multi-component system for making impressions according to claim 1, characterized in that said multi-component system further comprises (f) inhibitors of the condensation reactions of condensation catalysts or condensation cross-linking agents with compounds containing Si—OR structural units, wherein R=H, alkyl, alkoxyalkyl or acyl and the inhibitors of the condensation reactions (f) are di-, tri-, oligo- and -polydialkylsiloxanes of general formula $$Z—SiR^2—O—(SiR^2O)_n—SiR^3 \text{ or}$$

$$Z—SiR^2—O—(SiR^2O)_n—SiR^2—Z,$$

wherein Z is OH or $NR^{b\ 2}$, R represents the same or different optionally substituted hydrocarbyl residues, such as alkyl, alkenyl, aryl or alkynyl, and n=0 or an integer of from 1 to 100; or aliphatic diols, diamines, diphosphanes, polyamines, polyphosphanes or polyols, OH- , NH- or PR-functional polyethers or other chelating compounds.

9. A multi-component system for making impressions according to claim 1, characterized in that said multicomponent system further comprises water-donating agents (g) comprising inorganic fillers containing superficially bound residual moisture or water bound in the crystal lattice, zeolites, purposefully moistened fillers or organic substances having a defined water content.

10. A multi-component system for making impressions according to claim 1, characterized in that said multi-component system further comprises desiccants (h) comprising zeolites, dried fillers or water-absorbing organic compounds, such as oxazolidines and alkali salts of poly (meth)acrylic acid (superabsorbers).

11. A multi-component system for making impressions according to claim 1, characterized in that said multi-component system further comprises inert carrier materials (i) comprising mineral oils, branched hydrocarbons, vaseline, esters, phthalic acid esters, acetyltributyl citrate, polyalkylene oxides and polyesters and their copolymers.

12. A multi-component system for making impressions according to claim 1, characterized in that said multi-component system further comprises compounds for reaction inhibition of the hydrosilylation reaction (j) comprising short-chained organopolysiloxanes of general formula

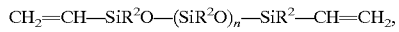

$$CH_2{=}CH{-}SiR^2O{-}(SiR^2O)_n{-}SiR^2{-}CH{=}CH_2,$$

wherein R represents the same or different optionally substituted hydrocarbyl residues, such as alkyl, alkenyl, aryl, alkynyl, alkenyl, and alkynyl-terminated siloxane residues; and n=0 or an integer of from 1 to 6; or vinyl-containing cyclic siloxanes, such as tetravinyltetramethylcyclotetrasiloxane, or organic hydroxy compounds containing terminal double or triple bonds, diethyl maleate, alkylsilane, arylsilane, alkenylsilane, alkynylsilane, benzotriazole, compounds comprising a 1,4-ene-yne structural unit, compounds comprising a 1,3-ene-yne structural unit, such as 2-methyl-1-hexene-3-yne, ethyl-3-(trimethylsilyl) propynoate, bis(phenylethynyl)dimethylsilane, diynes, such as decadiyne or dodecadiyne, polyynes, dienes, polyenes, such as decatriene, (1,3-dioxane-2-ylethynyl) trialkylsilane, 1,4-divinyltetramethyldisilylethane, amines or phosphanes.

13. A multi-component system for making impressions according to claim 1, characterized in that said multi-component system further comprises reinforcing fillers (k) comprising highly dispersed active fillers, such as titanium dioxide, aluminum oxide, zinc oxide, or wet-precipitated or pyrogenic silicic acid, which may optionally be in a hydrophilic or hydrophobized form; or mineral fibrous fillers, such as wollastonite; or synthetic fibrous fillers, such as glass gibers, ceramic fibers or plastic fibers.

14. A multi-component system for making impressions according to claim 1, characterized in that said multi-component system further comprises non-reinforcing fillers (1) comprising metal oxides, metal oxide hydroxides, mixed oxides or mixed hydroxides, or silica, in the form of quartz and its crystalline modifications, fused silica, alumina, calcium oxide, aluminum hydroxide, calcium carbonate, kieselguhr, diatomaceous earth, talcum, ground glasses and plastic-based fillers, for example, polymethyl methacrylate, polycarbonate, polyvinyl chloride, silicone resin powder, or powder based on fluoro-organic compounds, the non-reinforcing fillers optionally being surface-treated (coated).

15. A multi-component system for making impressions according to claim 1, characterized in that said multi-component system further comprises auxiliaries (m) comprising dyes, surfactants, opaque substances, matting agents, such as titanium dioxide or zinc oxide, plasticizers, hydrogen adsorbers/absorbers, radiopaque substances or organosilicon MQ resins comprising Si-vinyl, Si—OR, Si-ethynyl or SiH groups, or compounds or buffers and substances for adjusting the pH range.

16. Mixtures obtainable by mixing the components A and B of claim 2.

17. The mixtures according to claim 16, characterized in that, during and after the mixing of the components, the mixture, in a first step, undergoes a transition from a lighter-bodied mixer-suitable initial consistency to a heavier-bodied plastic phase in which the material builds up a high force pressure in the making of dental impressions in the impression tray, and in a second step, cures to its final elastic form.

18. The mixtures according to claim 16, characterized in that said mixtures have been cured to completion.

19. The mixtures according to claim 16, characterized in that the mixtures have a mixer-suitable consistency, in a first state at the beginning of mixing, of >26 mm (according to ISO 4823), whereupon the mixtures undergo transition to a heavier-bodied second state with a consistency of <35 mm (according to ISO 4823), caused by condensation reactions of SiOR groups or by hydrosilylation reactions of alkynyl groups with SiH groups, this latter consistency being maintained over a period of at least 15 s, and thereafter, the mixtures undergo transition to a third solid, elastic state following curing through a hydrosilylation reaction of alkenyl groups with SiH groups.

20. A method for the preparation of impressions from objects from which impressions are to be made using a multicomponent system according to claim 1, wherein the impression material is prepared by mixing the components, wherein the impression material is first dispensable in a first state from a container, whereupon it undergoes transition to a second state in which the viscosity of the impression material is increased, whereupon an impression is prepared from an object from which an impression is to be made, whereupon the impression material undergoes transition to a third, solid state in which an impression result is recorded, the second state being achieved by graded hydrosilylation reactions between alkynyl and alkenyl structural units with compounds containing Si—H groups and/or by graded addition reactions (between alkenyl and SiH groups) and condensation reactions (of SiOR groups with condensation catalysts).

21. The method according to claim 20, characterized in that, the consistency of the impression material in a first state at the beginning of mixing is >26 mm (according to ISO 4823), and the impression material is mixer-suitable in this first state, that the consistency of the impression material in the second state is <35 mm (according to ISO 4823), wherein the impression material is heavier-bodied than it is in the first state, and that the impression material in this second state is retained to the end of the total pot life, i.e., for at least 15 s.

22. The method according to claim 20, characterized in that, the mixtures have a mixer-suitable consistency, in a first state at the beginning of mixing, of >26 mm (according to ISO 4823), whereupon the mixtures undergo transition to a heavier-bodied second state with a consistency of <35 mm (according to ISO 4823), by a hydrosilylation reaction of alkenyl groups with SiH groups, this latter consistency being maintained over a period of at least 15 s, and thereafter, the mixtures undergo transition to a third solid, elastic state through condensation reactions of SiOR groups or through hydrosilylation reactions of alkynyl groups with SiH groups.

23. A multi-component system for making impressions which contains (a) at least one compound having at least two alkenyl groups;

(b) at least one orqanohydrogenpolysiloxane;

(c) at least one hydrosilylation catalyst;

characterized by containing one or both of components ($d_1$) and ($d_2$), wherein ($d_1$) is at least one polymeric compound having at least one alkynyl group characterized in that the alkynyl compound ($d_1$) is

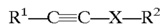

wherein $R^1$=alkyl, aryl, arylalkyl, halogen-substituted alkyl or aryl groups, cyanoalkyl, cycloalkyl, —H, alkoxy, acyl and combinations thereof;

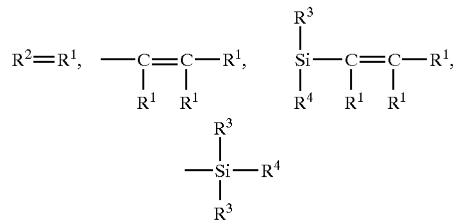

$R^3$=halogen, aryl, alkylaryl, H, halogen-substituted alkyl and aryl groups, alkyl, or combinations thereof;

$R^4$=$R^3$, or $R^4$ is alkyl, methyl, or combinations thereof;

X=polysiloxane, oligosilicic acid esters, polysilicic acid esters, polymeric or hydrocarbons copolymers of the above mentioned compounds;

and ($d_2$) is at least one compound having an Si—OR structural unit, wherein the Si—OR compound ($d_2$) is

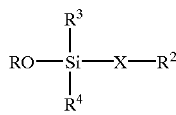

wherein

R=H, alkyl, alkoxyalkyl or acyl;

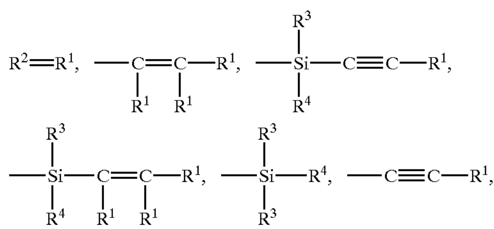

$R^1$=alkyl, aryl, arylalkyl, halogen-substituted alkyl or aryl groups, cyanoalkyl, cycloalkyl, cycloalkenyl, —H, acyl, or combinations thereof;

$R^3$=alkenyl, alkynyl, halogen, aryl, alkylaryl, H, halogen-substituted alkyl or aryl groups, alkyl, or combinations thereof;

$R^4$=$R^3$, or $R^4$ is different from $R^3$, wherein $R^4$ is alkyl, methyl, alkynyl, ethynyl, or combinations thereof; and X=polysiloxane, oligosilicic acid esters, polysilicic acid esters, polyethers, polymeric hydrocarbons, polyesters and copolymers of the above mentioned compounds; and when a compound ($d_2$) having an Si—OR structural unit is contained, (e) at least one condensation catalyst or condensation cross-linking agent; and (f) inert carrier materials selected from the group consisting of mineral oils, branched hydrocarbons, vaseline, esters, phthalic acid esters, acetyltributyl, citrate, polyalkylene oxides and polyesters and their copolymers.

24. A multi-component system for making impressions which contains (a) at least one compound having at least two alkenyl groups;

(b) at least one orqanohydrogenpolysiloxane;

(c) at least one hydrosilylation catalyst;

characterized by containing one or both of components ($d_1$) and ($d_2$), wherein ($d_1$) is at least one polymeric compound having at least one alkynyl group characterized in that the alkynyl compound ($d_1$) is

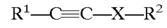

wherein $R^1$=alkyl, aryl, arylalkyl, halogen-substituted alkyl or aryl groups, cyanoalkyl, cycloalkyl, —H, alkoxy, acyl and combinations thereof;

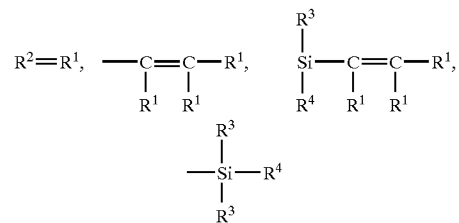

$R^3$=halogen, aryl, alkylaryl, H, halogen-substituted alkyl and aryl groups, alkyl, or combinations thereof;

$R^4$=$R^3$, or $R^4$ is alkyl, methyl, or combinations thereof;

X=polysiloxane, oligosilicic acid esters, polysilicic acid esters, polymeric hydrocarbons or copolymers of the above mentioned compounds;

and ($d_2$) is at least one compound having an Si—OR structural unit, wherein the Si—OR compound ($d_2$) is

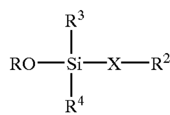

wherein

R=H, alkyl, alkoxyalkyl or acyl;

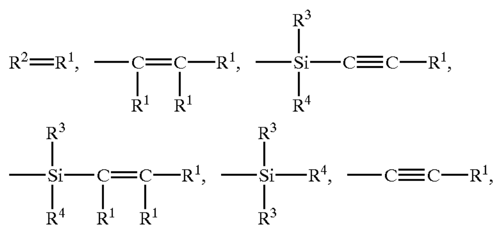

$R^1$=alkyl, aryl, arylalkyl, halogen-substituted alkyl or aryl groups, cyanoalkyl, cycloalkyl, —H, acyl, or combinations thereof;

$R^3$=alkenyl, alkynyl, halogen, aryl, alkylaryl, H, halogen-substituted alkyl or aryl groups, alkyl, or combinations thereof;

$R^4$=$R^3$, or $R^4$ is different from $R^3$, wherein $R^4$ is alkyl, methyl, alkynyl, ethynyl, or combinations thereof; and X=polysiloxane, oligosilicic acid esters, polysilicic acid esters, polyethers, polymeric hydrocarbons, polyesters and copolymers of the above mentioned compounds; and when a compound ($d_2$) having an Si—OR structural unit is contained, (e) at least one condensation catalyst or condensation cross-linking agent;

wherein said multi-component system comprises at least two components A and B, characterized in that component A contains (a) the at least one compound having at least two alkenyl groups; and (b) the at least one organohydrogenpolysiloxane; and ($d_1$) the at least one polymeric compound having at least one alkynykl, group or ($d_2$) the at least one compound having an Si—OR structural unit, wherein R=H, alkyl, alkoxyalkyl or acyl;

and component B contains (c) the at least one hydrosilylation catalyst; and when a compound ($d_2$) having an Si—OR structural unit is contained, component A, component B, or each of components A and B contains (e) the at least one condensation catalyst or condensation cross-linking agent; and wherein one or both of components A and B further contains (f) inhibitors of the condensation reactions of condensation catalysts or condensation cross-linking agents with compounds containing Si—OR structural units, wherein R=H, alkyl, alkoxyalkyl or acyl;

(g) water-donating agents;

(h) desiccants;

(i) inert carrier materials;

(j) compounds for reaction inhibition of the hydrosilylation reaction;

(k) reinforcing fillers;

(l) non-reinforcing fillers; and (m) auxiliaries.

* * * * *

UNITED STATES PATENT AND TRADEMARK OFFICE

CERTIFICATE OF CORRECTION

PATENT NO. : 7,005,460 B2
APPLICATION NO. : 10/053878
DATED : February 28, 2006
INVENTOR(S) : Bublewitz et al.

It is certified that error appears in the above-identified patent and that said Letters Patent is hereby corrected as shown below:

Column 25,
Line 7, after "($d_1$)" insert -- the --.
Line 12, after "(c)" insert -- the --.
Line 16, after "(e)" insert -- the --.

Column 28,
Line 49, after "that" delete ",".

Column 29,
Line 35, after "polymeric" change "or hydrocarbons" to -- hydrocarbons or --.

Signed and Sealed this

Twenty-seventh Day of June, 2006

JON W. DUDAS
*Director of the United States Patent and Trademark Office*